United States Patent [19]

von Weissenfluh

[11] Patent Number: 4,631,030
[45] Date of Patent: Dec. 23, 1986

[54] EQUIPMENT FOR PUTTING IN APPROXIMAL FILLINGS WITH LIGHT-HARDENING MATERIALS

[75] Inventor: Beat von Weissenfluh, Gentilino, Switzerland

[73] Assignee: Hawe-Neos Dental Dr. H. von Weissenfluh S.A., Gentilino, Switzerland

[21] Appl. No.: 746,058

[22] Filed: Jun. 18, 1985

[30] Foreign Application Priority Data

Jul. 9, 1984 [CH] Switzerland .................. 3301/84

[51] Int. Cl.⁴ .................................... A61C 7/00
[52] U.S. Cl. .............................. 433/149; 433/229
[58] Field of Search ................. 433/148, 149, 229

[56] References Cited

U.S. PATENT DOCUMENTS 3,815,243  6/1974  Eames .................... 433/149

4,449,928  5/1984  Weissenfluh ............ 433/229

Primary Examiner—Robert Peshock
Attorney, Agent, or Firm—Young & Thompson

[57] ABSTRACT

The equipment makes it possible to cause the polymerization of resin by light, starting from the approximal-apical zone (8') of the tooth, i.e., at the base of the filling. It comprises a wedge (1) transparent to the rays used for polymerization of the resin inserted in the approximal zone (i.e., between teeth), a wedge shaped to refract or reflect the concentrated light provided it by a lighting device equipped with a cap with a converging lens, in the axial direction, deflecting it and emitting it in the lateral direction (9'), so as to illuminate the filling resin with greater intensity at its base (8'), avoiding fissures (15) between the filling and base of the tooth, which would occur if the illumination were performed, as is now done (at 14) starting from the occlusal (masticatory) part of the tooth.

5 Claims, 6 Drawing Figures

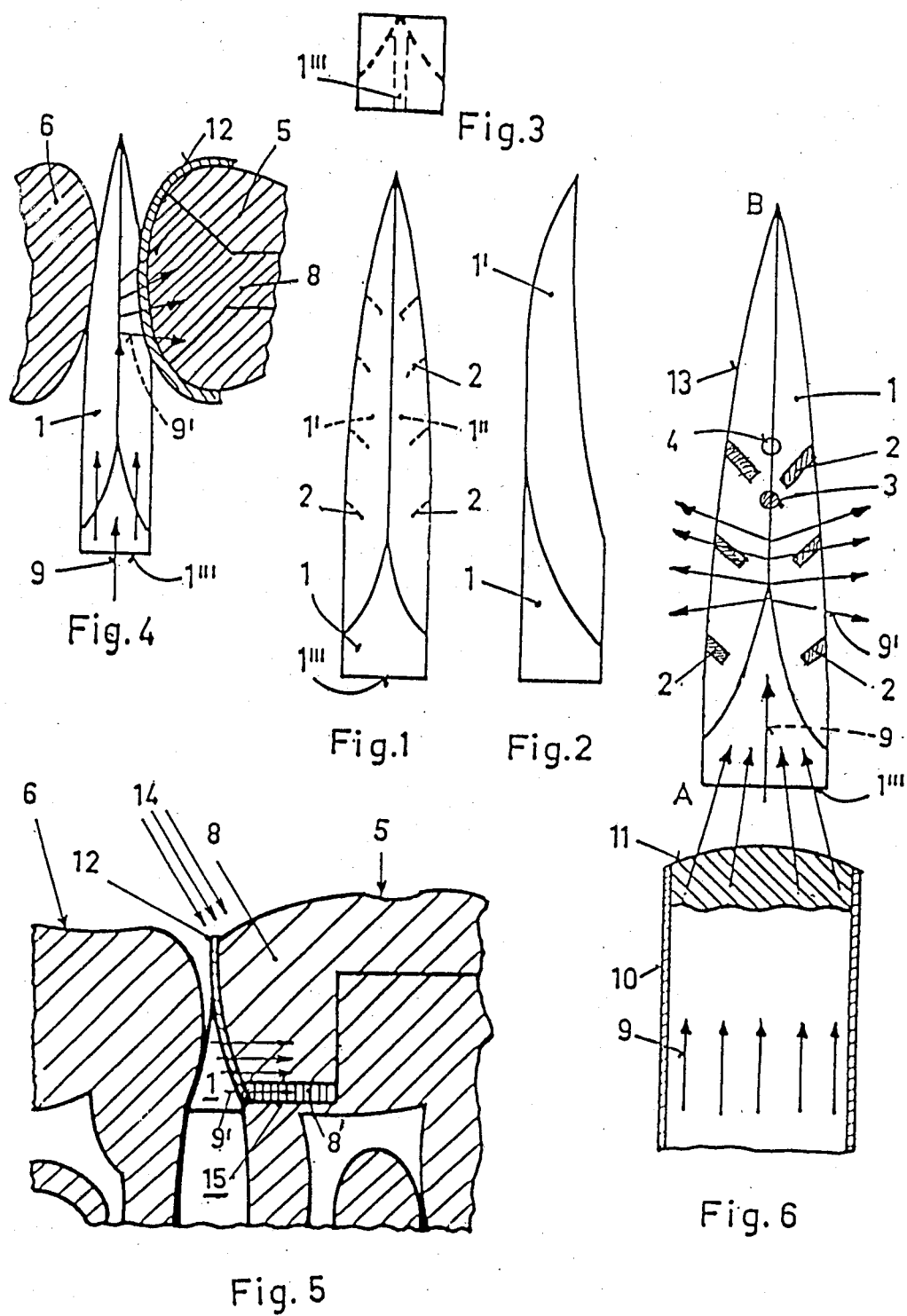

EQUIPMENT FOR PUTTING IN APPROXIMAL FILLINGS WITH LIGHT-HARDENING MATERIALS

It is known that recent advances in the field of dentistry are making possible the advantageous substitution of the amalgam used for filling teeth with the use, first of two-component resins hardening by interreaction and then of monocomponent resins polymerizable by illumination either with ultraviolet or visible light.

The technique normally used is that of applying, around the cavity to be filled, a transparent mold able to receive and hold the resin, introducing between the tooth to be filled and the adjacent one a wedge of wood or plastic that holds the mold in position and illuminating the filling from the occlusal, i.e., masticatory, part.

This technique creates serious problems in the case of class II fillings, i.e., occlusal-approximal fillings (fillings that comprise a masticatory, i.e., occlusal part of the tooth and a lateral, i.e., approximal, part of the tooth, where two adjacent teeth are proximate, i.e., neighboring), since the shape and size of the optical fiber conductors used in dentistry are such as to permit illumination only from the occlusal surface.

In this case, drawbacks are noted: axial illumination strikes the occlusal surface of the filling with greater intensity, an intensity that progressively weakens during penetration of the light in the strata of the resin by absorption by this latter; handening therefore begins from the occlusal surface of the tooth and spreads to the bottom of the filled cavity. Considering that the resin contracts when hardening (shrinking by polymerization), it happens that as the hardening spreads in depth a fissure develops between the hardened resin and the bottom of the cavity of the tooth, i.e., at the base of the filling.

This is extremely serious since the fissure that is created in time allows the infiltration and establishment of bacterial colonies, the cause of new caries.

The equipment according to this invention makes it possible to cause polymerization of the resin to occur in the approximal-apical stratum, i.e., starting from its zone of contact with the tooth at the base of the filling itself, avoiding fissures and the drawbacks described above.

According to a preferred embodiment, the wedge exhibits substantially triangular sections, decreasing from the base to the apex, passed through crosswise by bodies functioning as prisms and as reflecting bodies, cavities and surfaces suitable for refracting or reflecting the polymerizing light rays from the axial direction to that crosswise direction.

The wedge is preferably made of thermoplastic resins such as acrylic resins, polystyrene and the like.

In turn, the cap that can be applied to the final section of the optical fiber conductors preferably consists of an end shaped as a converging lens to concentrate all the light on the base of the wedge.

For greater clarity, the accompanying drawing represents some preferred nonlimiting embodiments of the equipment under discussion.

FIG. 1 represents the wedge seen in a top plan view;
FIG. 2 represents it in side view;
FIG. 3 represents it in front view;
FIG. 4 represents it in a top plan view, inserted between two teeth at the time of putting in an approximal filling;
FIG. 5 represents it in cross section during putting in the filling mentioned in FIG. 4;
FIG. 6 represents, in top plan view, the equipment under discussion comprising the transparent wedge mentioned above and the cap that can be applied with the converging lens that illuminates it.

With reference to the various figures:

wedge 1 (FIGS. 1 and 2), made of transparent thermoplastic resins, such as acrylic resins, polystyrene, or other suitable transparent materials, exhibits two sides 1', 1" which are slightly concave to fit the transparent mold in an anatomically correct manner to the tooth and to facilitate its introduction between two teeth 5 and 6 (FIGS. 4 and 5) of which tooth 5 is to be filled at 8 with a resin that is light-polymerizable.

Front surface 1''' of the wedge, which holds transparent mold 12 delimiting filling 8, axially receives (FIG. 4) light rays 9 supplied by a lighting apparatus provided, according to the invention, with an applicable cap 10 (FIG. 6); these rays are deflected laterally to 9' either by reflection by metallic or nonmetallic reflecting bodies 3 or by cavities 4 or transparent prisms 2 buried in the transparent material making up the wedge itself, or by reflection if surface AB is reflective, e.g., metallized.

Since wedge 1 is at the base of filling 8 (see FIG. 5), lateral light rays 9' which it emits strike lower stratum 8' (being at FIG. 5) of filling 8, i.e., they strike the stratum which is at the base of the filling itself and thus cause hardening of the resin starting precisely from this lower zone: a hardening that progressively spreads upward, or better, to the occlusal (masticatory) part, affecting the entire filling. Illumination with upper occlusal rays 14 can optionally accelerate the polymerization.

Thus, formation of a fissure at 15 is avoided which would occur if hardening were performed starting from the occlusal surface toward the bottom of the cavity to be filled (still being at FIG. 5), a fissure that in time would allow infiltration and establishment of bacterial colonies, a cause of formation of new caries.

FIG. 6 shows the cap that can be applied to the final section of optical fiber conductors for illumination of wedge 1, ending in a convex surface 11, acting as a lens converging axial rays 9 so as to affect the entire front surface 1''' of the wedge.

It is provided that surface AB of the wedge. i.e., surface 13 located in the part opposite that in which filling 8 is located, can be silver-plated to contribute to reflecting to the filling itself.

The shape of the wedge, that of the bodies inserted in it to refract or reflect axial light 9 to deflect it to 9', and also the material that constitutes said bodies, can be any kind, provided they are within the scope of protection of the patent.

I claim:

1. Equipment for putting in approximal fillings (between teeth) with light-hardening materials, comprising a wedge (1) transparent to the rays used and adapted to be inserted between the teeth, the wedge having means to refract or reflect concentrated light supplied to it in the axial direction (9) by a light source (10), by deflecting it in the lateral direction (9'), so as to illuminate the filing material (8) with the greatest possible intensity in the approximal part of the cavity, making possible hardening of the filling material starting from the approximal-apical stratum (8').

2. Equipment according to claim 1, wherein said wedge (1) exhibits substantially triangular sections, decreasing from the base to the apex, passed through crosswise by bodies (2) functioning as prisms and reflecting bodies (3), cavities and surfaces (4) able to refract or reflect the hardening light rays from the axial to the crosswise direction.

3. Equipment according to claim 1, wherein said wedge (1) is made of thermoplastic resins such as acrylic resins, polystyrene and the like, which can be hardened by polymerization.

4. Equipment according to claim 1, wherein said lighting apparatus exhibits its end equipped with emitter (10) concentrating all the light rays on the base (1''') of the wedge (1).

5. Equipment as in claim 4, where said light emitter consists of a cap that can be applied to the final section of the optical fibers of the lighting apparatus, with the end shaped like a converging lens (11).

* * * * *